United States Patent

Siegel et al.

[11] Patent Number: 6,113,570
[45] Date of Patent: *Sep. 5, 2000

[54] METHOD OF REMOVING THROMBOSIS IN FISTULAE

[75] Inventors: Robert J. Siegel, Venice, Calif.; Robert E. Carter, Arlington, Mass.

[73] Assignee: Coraje, Inc., San Francisco, Calif.

[ * ] Notice: This patent is subject to a terminal disclaimer.

[21] Appl. No.: 08/854,911

[22] Filed: May 13, 1997

Related U.S. Application Data

[63] Continuation-in-part of application No. 08/441,127, May 15, 1995, Pat. No. 5,695,460, which is a continuation-in-part of application No. 08/303,858, Sep. 9, 1994, Pat. No. 5,509,896.

[51] Int. Cl.⁷ ..................................................... A61M 31/00
[52] U.S. Cl. .................................. 604/52; 601/2; 604/49; 604/28
[58] Field of Search ................................. 604/49, 28, 21, 604/22, 27, 52, 53; 601/2, 3

[56] References Cited

U.S. PATENT DOCUMENTS 5,318,014  6/1994  Carter ........................................ 604/22
5,695,460  12/1997  Siegel et al. ............................. 604/21

Primary Examiner—Wynn Wood Coggins
Assistant Examiner—Jennifer R. Sadule
Attorney, Agent, or Firm—Walter A. Hackler

[57] ABSTRACT

Apparatus and methods are provided for utilizing a combination of ultrasonic energy and an echo contrast agent containing microbubbles, for substantially dissolving blood clots or other fistula obstructions. One embodiment of the present invention alternatively utilizes a selected dose of thrombolytic agent in combination with an echo contrast agent, for enhancing the thrombolytic action of a thrombolytic agent and removing a thrombosis from a fistula.

13 Claims, 1 Drawing Sheet

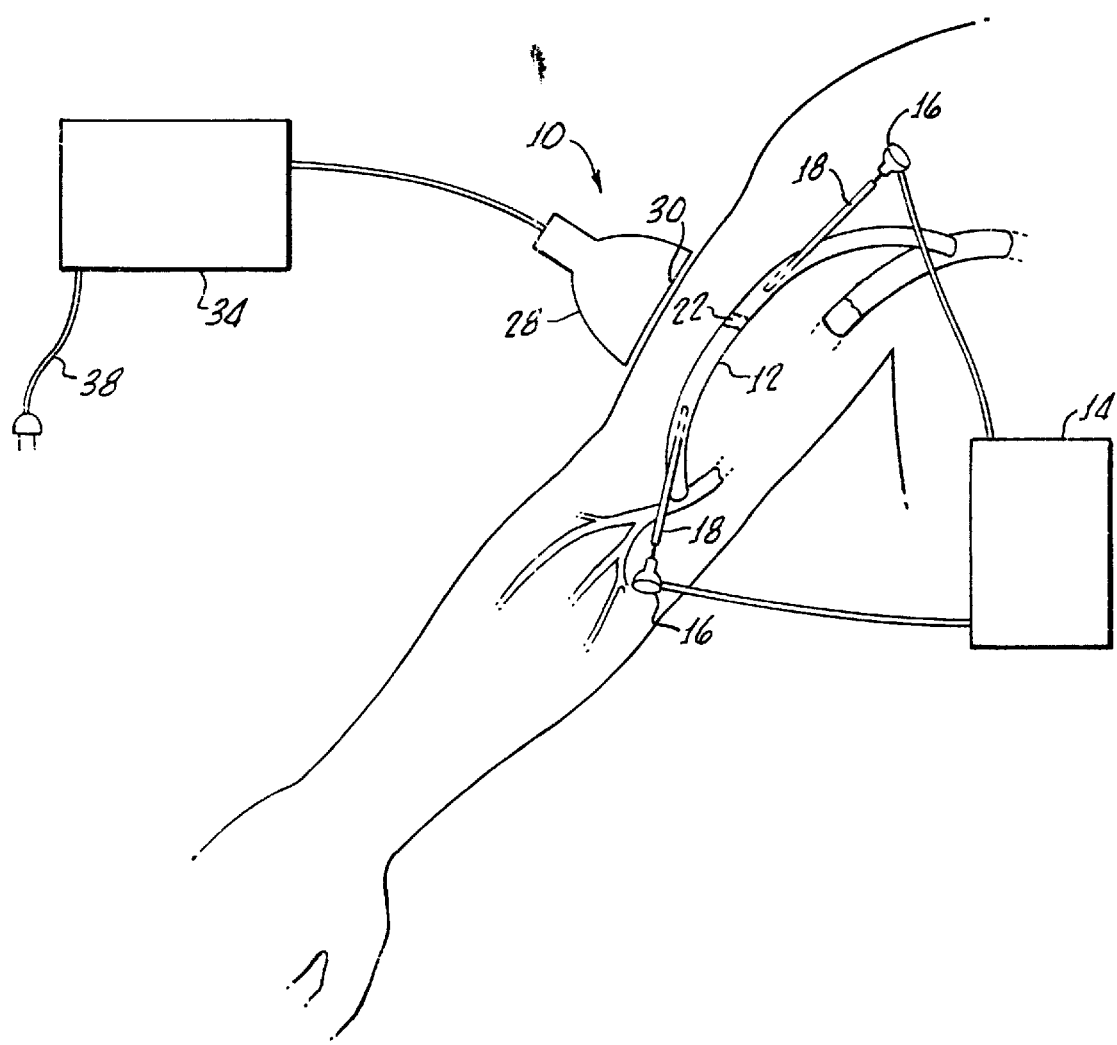

METHOD OF REMOVING THROMBOSIS IN FISTULAE

The present application is a continuation-in-part of U.S. Ser. No. 08/441,127, filed May 15, 1995, now U.S. Pat. No. 5,695,460, which is a continuation-in-part of U.S. Ser. No. 08/303,858, filed Sep. 9, 1994, now U.S. Pat. No. 5,509,896.

The present invention is generally related to the use of ultrasonic energy and is more particularly directed to the use of ultrasound with ultrasound imaging agents, alone or in combination with thrombolytic agents, to dissolve thrombosis in a fistula.

It is known that ultrasound imaging can be used to locate intravascular thrombi and it has been demonstrated that the utilization of ultrasonic waves can improve the diffusion and penetration of medicinal fluids or the like into the vascular system (see U.S. Pat. No. 5,197,946 to Tachibana). Tachibana teaches that in order to effectively enhance or improve the diffusion and penetration or a medicinal fluid, the oscillating element must be disposed at the point of injection of the medicinal fluid.

This is to be contrasted, according to Tachibana, with prior art techniques which utilize ultrasonic waves and a catheter wire for diffusion and penetration of medicinal fluids. In this arrangement the ultrasonic oscillating element is connected to the catheter site outside the body and far from a radiating end of the catheter wire. This results in a significant reduction in efficient coupling of the ultrasound due to the damping of ultrasonic energy in the course of transmission down the catheter wire.

Other disadvantages in the use of a transmission wire to deliver ultrasonic energy to a thrombosis is transmission wire stiffness. Further, as the transmission wire diameter is reduced to lower the stiffness thereof, it is more difficult to deliver sufficient energy for effective removal of the thrombosis. To overcome these disadvantages, miniature ultrasonic ablation tools have been developed, utilizing ultrasonic transducers sized for arterial insertion. While these devices overcome the transmission wire difficulties, their small size severely limits the amount of ultrasonic energy available for direct mechanical action for fragmenting plaque and thrombosis and/or energy for improving diffusion and penetration of medicinal fluids as described in U.S. Pat. No. 5,197,946.

Ultrasonic apparatus have also been utilized to assist in the delivery of medicaments in specific areas of a vein. For example, U.S. Pat. No. 5,040,537 to Katakura teaches the use of injecting numerous fine capsules, with an agent being packed therein, into a patient's body and thereafter applying a shock wave to provide dominant positive pressure from outside the body to rupture the capsules dispersed in the body.

Thus, ultrasonic energy in the form of a pulsated shock wave is generated exterior to the body and imaged to selectively burst agent-containing capsules in order to selectively release the agent into the blood.

The present invention is directed to the discovery that ultrasound itself, or in combination with a diagnostic medium, particularly echo contrast agents containing microbubbles, utilized in conjunction with ultrasound, provides a safe and effective method for dissolving fistula thrombi with and without the use of thrombolytic drugs.

This is important, since long-term vascular access is required in all hemodialysis patients in order to achieve blood flow rate sufficient for removal of metabolic by-products such as, for example, urea, creatinine, and other nitrogenous compounds, along with excess plasma water.

Generally speaking, there are two principal types of permanent vascular access for hemodialysis, namely, endogenous arteriovenous fistula, commonly known as a shunt, and a synthetic polytetrafluoroethylene (PTFE) arteriovenous graft, which is preferably placed in a distal upper extremity.

The arteriovenous fistula is preferred because of fewer complications arising with long-term use. However, a large number of patients who require a long-term hemodialysis do not have blood vessels suitable for the creation of an autogenous fistula.

Unfortunately, an inescapable relationship exists between the use of a PTFE graft as a dialysis access and thrombosis.

Stenosis affecting the graft, its anastomoses, and draining veins, i.e., venous stenosis, is the primary cause of thrombosis and this occurs with high frequency.

A common therapy in dialysis units for a thrombosis graft is surgery. Surgery is effective in restoring flow in the graft, however, it has a number of disadvantages.

First, surgery is, by nature, invasive, which results in considerable blood loss and may require a general anesthesia. Common pain and discomfort immediately occurs and for several days afterwards, and frequently requires hospitalization. Naturally, there is also a significant risk of infection.

This, in turn, may cause delayed or missed dialysis treatments and consequently requires central venous dialysis catheters.

Ultimately, more extensive surgery by way of a replacement graft ultimately results in the loss of potential access sites. Since this problem is recurrent, continued graft replacement eventually results in the elimination of most, if not all, access sites in a patient.

Consequently, there is need for a rapid, safe, effective and minimally evasive out-patient procedure for restoration of graft function, which would allow the patient to be quickly returned to the dialysis unit for timely effective treatment. The present invention is directed to a method and apparatus suited to fill that need.

SUMMARY OF THE INVENTION

A method in accordance with the present invention utilizes the discovery of the effectiveness of applying a combination of ultrasonic energy and certain agents, including ultrasound imaging agents, to dissolve arterial thrombi. Particularly, the present invention includes a method for substantially reducing and removing a thrombosis disposed within a body vessel, particularly, a fistula, by radiating an ultrasound imaging agent, particularly a microbubble containing echo contrast agent, and/or a thrombolytic agent, proximate the thrombosis shunt or PTFE graft, with ultrasound. The ultrasound may be applied transcutaneously by means of an external generator and transducer. Importantly, the introduction of a thrombolytic agent proximate the thrombosis further enhances the clot dissolution capability of a method in accordance with the present invention. This step is carried out during thrombolytic action by the thrombolytic agent on the thrombosis disposed within the graft.

This method is clearly distinguished from prior art techniques such as taught by Katakura in U.S. Pat. No. 5,040,537, in which ultrasound generated exterior to the body vessel is used only to rupture capsules containing an active agent. Clearly, the prior art is specifically directed to the release of an active agent within a vessel, whereas the present invention is directed to introduction of a microbubble media that does not contain an active agent, in order to enhance the effect of ultrasound in removal of thrombosis and increase the effect of a thrombolytic agent during its activity in dissolving, or splitting up, a thrombus. The present invention involves a phenomena of long and short range ultrasound enhancement of inherent drug activity.

In accordance with one embodiment of the present invention, a selected dose of a thrombolytic agent or an echo contrast agent is injected into an occluded vessel, and ultrasonic energy is radiated from an external source into the echo contrast agent transcutaneously. It has been found that at certain frequencies of ultrasonic radiation, the thrombosis is substantially dissolved using this combination of steps. This embodiment of the present invention is based on the discovery that the use of echo contrast agents, particularly microbubble medium, substantially increases the effectiveness of ultrasound therapy in removing cardiovascular blockages. The echo contrast agent may be used alone or in combination with a thrombolytic agent.

By way of specific example only, the echo contrast agent may be a perfluorocarbon, such as, for example, a dodecafluoropentane colloid dispersion, and the ultrasound may be introduced at a frequency of between about 24 kHz and about 53 kHz.

One embodiment of the present invention includes the step of introducing an echo contrast agent alone, proximate the thrombosis, and subsequently directing ultrasound into the thrombosis and proximate echo contrast agent, in order to substantially dissolve the thrombosis without the use of thrombolytic agents. The echo contrast agent may be one of several presently available types containing microbubbles and currently marketed for ultrasound diagnostic purposes, such as dodecafluoropentane (under trademark "Echogen"), and sonicated albumin (under trademark "Albumex").

The present invention also encompasses the enhancement, or acceleration, of the activity of a thrombolytic agent, and in that regard includes the steps of introducing a selected dose of an echo contrast agent and thrombolytic agent, proximate to a thrombosis disposed in a fistula and radiating the thrombosis with ultrasound in order to effect removal of the thrombosis in less time than required by activity of the selected dose of thrombolytic agent without ultrasound radiation of the thrombosis.

In other words, the present invention for enhancing thrombolytic action of a thrombolytic agent includes the steps of injecting a combination of echo contrast agent and thrombolytic agent or disruptive agent, proximate a thrombosis in a fistula, and providing transcutaneous or intravascular application of ultrasound proximate the thrombosis, with sufficient energy to increase the thrombolytic action of the thrombolytic agent.

The present invention, therefore, also encompasses a method for removing a cardiovascular obstruction and in that regard includes the steps of delivering an echo contrast agent, alone or in combination with a thrombolytic agent, proximate a cardiovascular obstruction disposed in a fistula and directing ultrasound at the cardiovascular obstruction with proximate agents, of sufficient energy to remove the cardiovascular obstruction from the fistula.

More particularly, in accordance with the present invention, the thrombolytic agent introduced may be any agent having suitable activity, such as, for example, streptokinase, staphlokinase, urokinase or a tissue plasminogen activator (TPA). These agents are set forth herein only by way of example and it should be appreciated that, as hereinabove recited, any thrombolytic agent has possible use in accordance with the present invention.

Additionally, the radiation by ultrasound may include continuous or pulsed radiation. Still more particularly, by way of specific example only, the amount of streptokinase introduced may be in concentrations of less than about 2,000 u/ml.

In conjunction with the hereinabove enumerated method defining the present invention, also encompassed is an apparatus for the removal of a blockage which, in combination, includes ultrasonic means for radiating a blockage disposed within a fistula and means for introducing selected dose of an echo contrast agent proximate the blockage in order to enhance the effect of the ultrasound in removing the blockage.

Clearly, the prior art teaches away from this discovery since prior art workers only were able to obtain enhancement for release of thrombolytic drugs within a vessel by introduction of ultrasound alone, which was thought to be due to mechanical agitation of surrounding vessel walls, as pointed out by Tachibana in U.S. Pat. No. 5,197,946. It must be accepted that the mechanism taught by the Tachibana reference is not applicable to the present discovery in which it has been found that the introduction of an echo contrast agent proximate thrombosis, and subsequent ultrasonic radiation of the agent and thrombosis, substantially dissolves thrombi, with or without the use of thrombolytic agents.

BRIEF DESCRIPTION OF THE DRAWINGS

The advantages and features of the present invention will be better understood by the following description when considered in conjunction with the accompanying drawings in which:

FIG. 1 is a diagram of ultrasonic surgical apparatus in accordance with the present invention or teaching method for removing a thrombosis, as well as enhancing the thrombolytic action of a thrombolytic agent in a fistula.

DETAILED DESCRIPTION

Turning now to FIG. 1, there is shown apparatus 10 in accordance with the present invention for both enhancing the effectiveness of ultrasound in removing a thrombosis and for enhancing thrombolytic action of a thrombolytic agent in a fistula, or PTFE graft, 12, which may include a supply 14 of a selected dose of an echo contrast agent alone or in combination with a thrombolytic agent which, by way of valves 16 and catheters 18, provides a means for injecting, introducing and delivering the agents, to the fistula 12, proximate a thrombosis 22 represented by the dashed lines in FIG. 1. It should be appreciated that the Figure is representative and as such should be considered to be either an autogenous fistula or a prosthetic graft fistula or equivalent arrangement.

Alternatively, the agents can be introduced or injected into the fistula 18 proximate the thrombosis 22 in any conventional manner, including, for example, hypodermic needle or the like (not shown).

Also shown in FIG. 1 is a transducer 28 having a surface 30 positioned exterior to the fistula 12 and interconnected to an oscillator/driver 34 which provides means for radiating the thrombosis, or blockage, 22 with ultrasound in order to effect removal thereof. In this embodiment of the present invention, the ultrasound is transmitted transcutaneously and thus the step of radiating ultrasound is a "non-invasive" procedure.

The ultrasonic transducer 28 may be of any conventional design with a frequency range of about 19 kHz to about 1

MHz, the frequency being manually adjustable for transmitting ultrasonic frequency through the surface 30. The frequency range may be limited to a range of between about 20 kHz and about 500 kHz if desired.

The surface 30 provides means for coupling the ultrasound with the fistula 12, thus enabling application of the ultrasound. It should be appreciated that the surface 30 can include means for focusing the ultrasound as may be required in order to concentrate or specifically direct the ultrasound to a desired area or volume.

The driver 34 is powered through conventional 110 volt line 38 and may have a power output of up to, for example, about 50 watts through a tip active area of about 0.75 inches by 0.75 inches. The power levels obtainable from the ultrasonic transducer 28 are capable of producing violent cavitation in tap water at atmospheric pressure and the limiting factor of introducing ultrasonic power into the body 20 would be possible skin irritation despite the output capability of the device. The driver 34 and transducer may be operated at a duty cycle of 100%, i.e., continuous output, or pulse-operated at, for example, a 50% duty cycle.

Alternately, ultrasound may be transmitted intravascularly, rather than transcutaneously as hereinabove described. For example, a miniature ultrasonic transducer (not shown) such as the device described in U.S. Pat. No. 5,269,291, incorporated herein by reference, may be utilized as a means for transmitting ultrasonic energy directly into and proximate the thrombosis 22 and surrounding vascular fluid. The miniature ultrasonic transducer 40 may be inserted into the fistula 12 by means of catheter 18.

It should be appreciated that ultrasound may be generated from driver 34 and transmitted therefrom via a guide wire (not shown) directly into the fistula 12.

In accordance with one embodiment of the present invention, the apparatus 10 is useful in the method of the present invention for removing a thrombosis, in which a selected dose of thrombolytic agent is introduced proximate the thrombosis 22 disposed within a fistula 12. The thrombosis 22 is radiated with ultrasound generated exterior to the body 20, or intravascularly as described above, to effect removal of the thrombosis 22 in less time than required by activity of the selected dose of thrombolytic agent without the ultrasound radiation of the thrombosis. Specific examples of this method will be shown in the examples following.

Another embodiment of the present invention includes introduction of an echo contrast agent alone, by means of the supply 14 or other conventional manner, into the fistula 12 at a position proximate the thrombosis 22, and subsequently radiating ultrasound into the thrombosis 22. It has been found that the introduction of an echo contrast agent, in combination with the ultrasonic energy radiated into the site of the thrombosis, will substantially increase the effectiveness of ultrasound in removing the thrombosis. This embodiment provides for substantial dissolution of the thrombosis without the need for the introduction of thrombolytic agents.

Importantly, it has been found that when ultrasound is applied at a lower, rather than a higher frequency, the effectiveness of the method is markedly enhanced. More particularly, when ultrasound is applied at less than about 100 kHz, and even more particularly, between approximately 25 kHz and approximately 53 kHz, the dissolution of thrombi is most significant. For example, at the frequency of about 53 kHz, the synergistic effect of a combination of ultrasound and echo contrast agent was most evident when compared to utilizing ultrasound alone.

More particularly, the echo contrast agent may be one of several types of microbubble media presently utilized for diagnostic ultrasound. Echo contrast agents can generally be classified into five groups: free gas bubbles, stabilized gas bubbles, colloidal suspensions, emulsions, and aqueous solutions. The aqueous solutions include aqueous solutions of air-filled proteinaceous microbubbles. Currently available products include gas filled liposomes, gas filled lipid bilayers, microbubbles containing liquids, gas emulsions, gas-filled microspheres and microbubbles containing suspensions.

Preferably, the echo contrast agent comprises dodecafluropentane, a colloidal suspension, for example, the agent presently marketed under the trademark "Echogen". Alternatively, sonicated human serum albumin, an aqueous solution, may be introduced as the echo contrast agent.

It is important to recognize that control experiments, which tested the effect on blood clots of an echo contrast agent, without ultrasound, have shown an absence of significant clot dissolution. It has also been found that high intensity, low frequency ultrasound does have an effect on clot dissolution. Importantly, a method in accordance with the present invention utilizes the surprising discovery that a combination of echo contrast agent and ultrasound, provides for effectively reducing or removing a thrombosis in less time than required by ultrasound radiation of the thrombosis without the use of said echo contrast agent. This may be due to the effect of microbubbles within the echo contrast agent that, when combined with ultrasonic energy, leads to increased cavitation of vascular fluid surrounding the thrombosis.

Another embodiment of the present invention includes the introduction of an echo contrast agent into the fistula 12 proximate the thrombosis 22, in order to increase the effectiveness of both a thrombolytic agent and ultrasound in removing the thrombosis. Preferably, the method includes the introduction of streptokinase as a thrombolytic agent into the fistula 12. As will be specifically set forth in the examples, the ultrasound may be continuously introduced or introduced in pulses, whereas the streptokinase may be introduced at concentrations of less than about 2,000 ul/ml.

In some instances, the method of the present invention not only provides enhancement, or acceleration, of the activity of the thrombolytic agent but also provides for removal of a thrombosis, utilizing a combination of ultrasound, echo contrast agent and thrombolytic agent, which otherwise cannot be removed through the use of a thrombolytic agent by itself. Specific examples of the use of the apparatus and agents are set forth in parent application Ser. No. 08/441,127 and U.S. Pat. No. 5,509,896 and are to be incorporated herein, including all referenced drawings by this specific reference thereto.

Although there has been hereinabove described a specific arrangement of ultrasonic apparatus and a method for thrombi dissolution in accordance with the present invention, for the purpose of illustrating the manner in which the invention may be used to advantage, it should be appreciated that the invention is not limited thereto. Accordingly, any and all modifications, variations, or equivalent arrangements which may occur to those skilled in the art, should be considered to be within the scope of the present invention as defined in the appended claims.

What is claimed is:

1. A method for removing a thrombosis in a fistula, said method comprising the steps of:

radiating a thrombosis, disposed in a fistula, with ultrasound in order to effect removal of the thrombosis by dissolution thereof, said ultrasound being introduced at a frequency of less than about 100 kHz; and introducing a selected dose of an echo contrast agent proximate the thrombosis in said fistula in order to enhance the effectiveness of the ultrasound in removing the thrombosis by dissolution thereof.

2. The method according to claim 1 wherein the echo contrast agent is comprised of a microbubble medium.

3. The method according to claim 2 wherein the microbubble medium is comprised of a medium selected from the group consisting of free gas bubbles, stabilized gas bubbles, colloidal suspensions, emulsions and aqueous solutions.

4. The method according to claim 2 wherein the microbubble medium is a colloidal suspension comprising dodecafluropentane.

5. The method according to claim 2 wherein the microbubble medium is an aqueous solution comprised of sonicated albumin.

6. The method according to claim 1 wherein the ultrasound is introduced at a frequency of between about 24 kHz and about 53 kHz.

7. A method for enhancing thrombolytic action of a thrombolytic agent, said method comprising the steps of:

radiating a thrombosis, disposed in a fistula, with ultrasound in order to effect removal of the thrombosis, said ultrasound having a frequency of less than about 100 kHz; and introducing a selected dose of a thrombolytic agent proximate the thrombosis in said fistula.

8. The method according to claim 7 wherein streptokinase is introduced as the thrombolytic agent.

9. The method according to claim 7 further comprising the step of introducing a selected dose of an echo contrast agent proximate the thrombosis in said fistula in order to enhance the effectiveness of both the ultrasound and the thrombolytic agent in removing the thrombosis.

10. The method according to claim 9 wherein the echo contrast agent is comprised of a microbubble medium.

11. The method according to claim 10 wherein the microbubble medium is comprised of a medium selected from the group consisting of free gas bubbles, stabilized gas bubbles, colloidal suspensions, emulsions and aqueous solutions.

12. The method according to claim 10 wherein the microbubble medium is a colloidal suspension comprising dodecafluropentane.

13. The method according to claim 10 wherein the microbubble medium is an aqueous solution comprising sonicated albumin.

* * * * *